United States Patent [19]

Morris

[11] Patent Number: 4,974,604
[45] Date of Patent: Dec. 4, 1990

[54] SURGICAL DRAPE WITH FLUID COLLECTION SYSTEM

[75] Inventor: H. Krzewinski Morris, Arlington, Tex.

[73] Assignee: Johnson & Johnson Medical Inc., Arlington, Tex.

[21] Appl. No.: 272,666

[22] Filed: Nov. 17, 1988

Related U.S. Application Data

[63] Continuation of Ser. No. 115,012, Oct. 29, 1987, abandoned.

[51] Int. Cl.$^5$ ............................................. A61B 19/08
[52] U.S. Cl. ..................................... 128/853; 128/855
[58] Field of Search .............................. 128/849–856

[56] References Cited

U.S. PATENT DOCUMENTS

| | | | |
|---|---|---|---|
| 3,494,356 | 2/1970 | Melges | 128/849 |
| 3,589,365 | 6/1971 | Sejman | 128/849 |
| 3,677,266 | 7/1972 | Green | 128/853 |
| 3,721,234 | 3/1973 | Hadtke | 128/852 |
| 3,942,523 | 3/1976 | Rudtke | 128/853 |
| 4,033,341 | 7/1977 | Scriuens | 128/852 |
| 4,040,418 | 8/1977 | Collins | 128/852 |
| 4,089,331 | 5/1978 | Hartigan | 128/853 |
| 4,169,472 | 10/1979 | Morris | 128/854 |
| 4,253,451 | 3/1981 | Solomon | 128/856 |
| 4,323,062 | 4/1982 | Canty | 128/852 |
| 4,462,396 | 7/1984 | Wichman | 128/853 |
| 4,489,720 | 12/1984 | Morris | 128/853 |
| 4,559,937 | 12/1985 | Vinson | 128/853 |
| 4,598,458 | 7/1986 | McAllester | 128/853 |
| 4,745,915 | 5/1988 | Enright | 128/853 |

Primary Examiner—Robert A. Hafer
Assistant Examiner—M. Brown

[57] ABSTRACT

A surgical drape having a main sheet and a fluid collection system for collecting and draining away from the site of surgery substantial quantities of irrigating liquids. The fluid collection system has a bag means and a pair of fluid directing elements portions of which are secured to the drape in spaced-apart relationship near the primary operative area and remainder portions of which are secured to portions of the periphery of the bag. In one preferred embodiment, the fluid collection system is made by suitably folding and appropriately securing a single sheet of liquid impervious material. The main sheet is preferably a nonwoven fabric. The liquid impervious sheet is preferably polyethylene. The fluid directing elements may have adhesive strips at their ends by which to secure the fluid collection system to a limb of a patient. The surgical drape may include a fenestrated region and having clipping tabs and tubing holders. The drape is particularly suited for use in arthroscopic surgery of the knee.

25 Claims, 7 Drawing Sheets

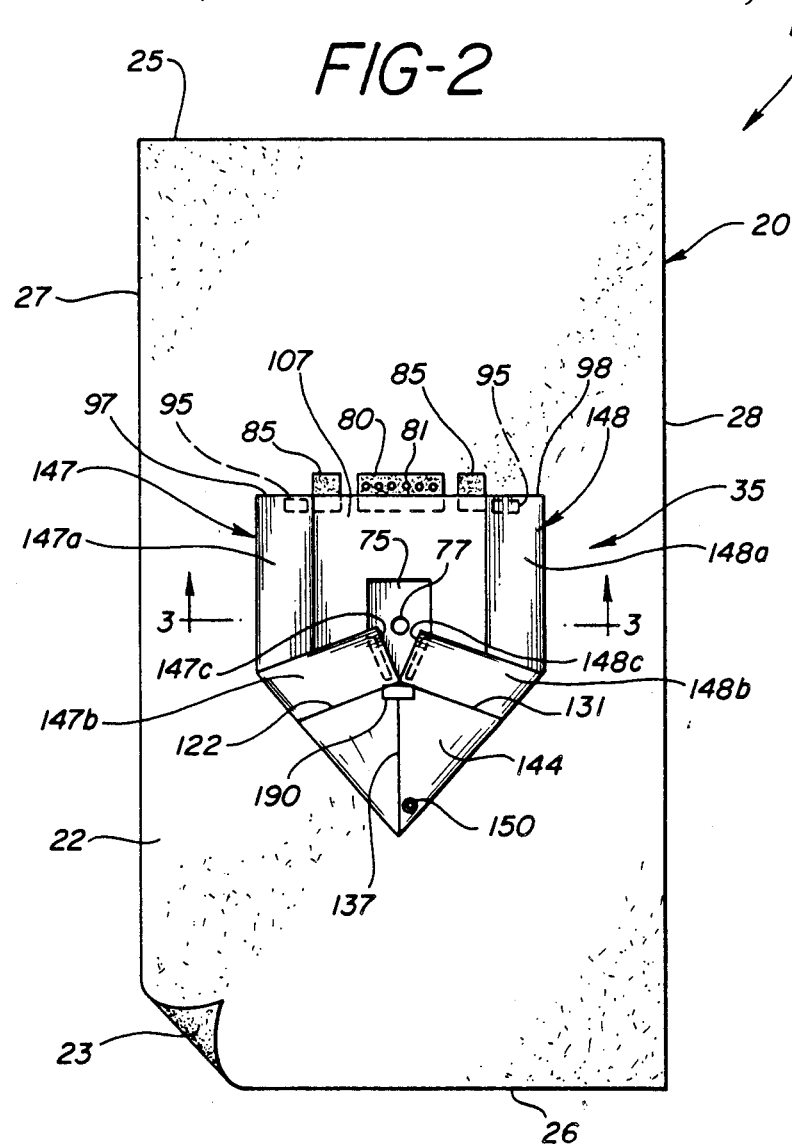
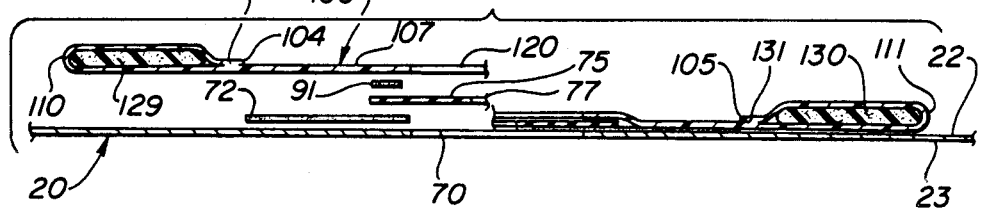

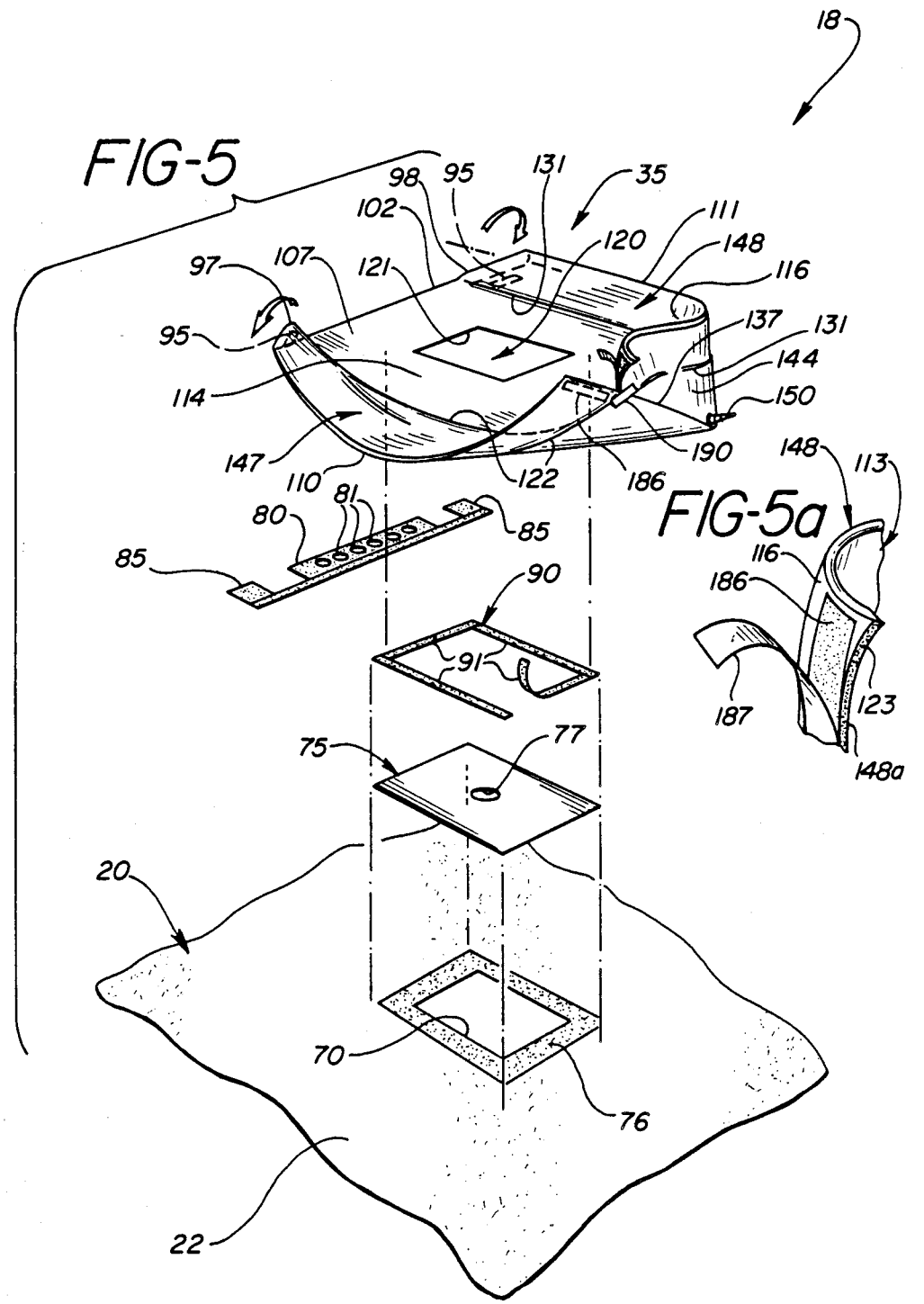

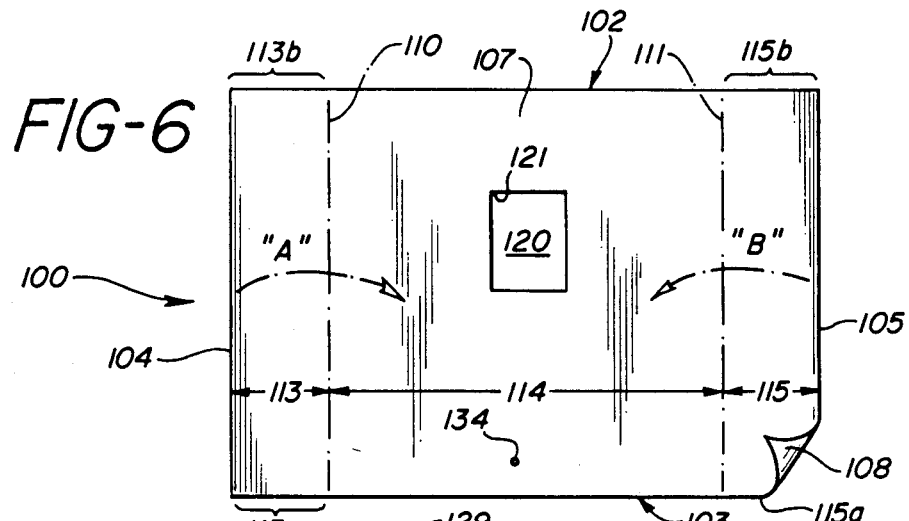
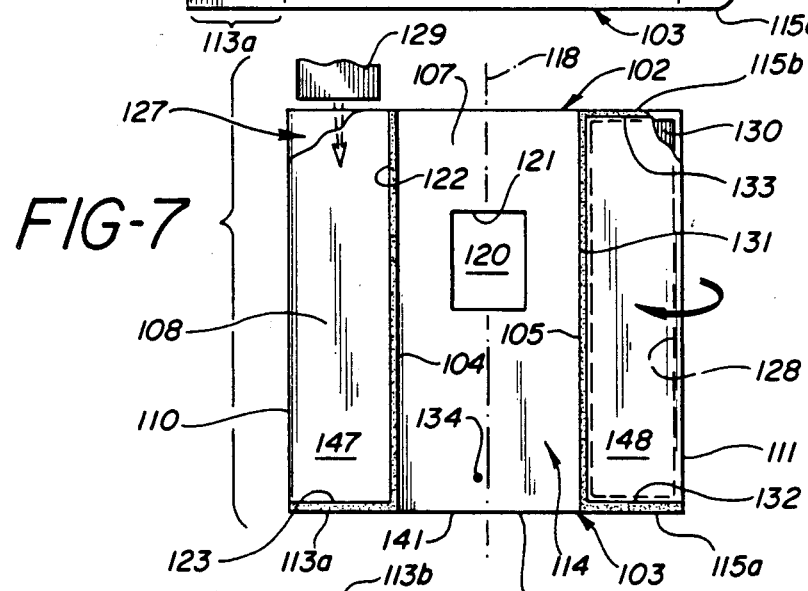
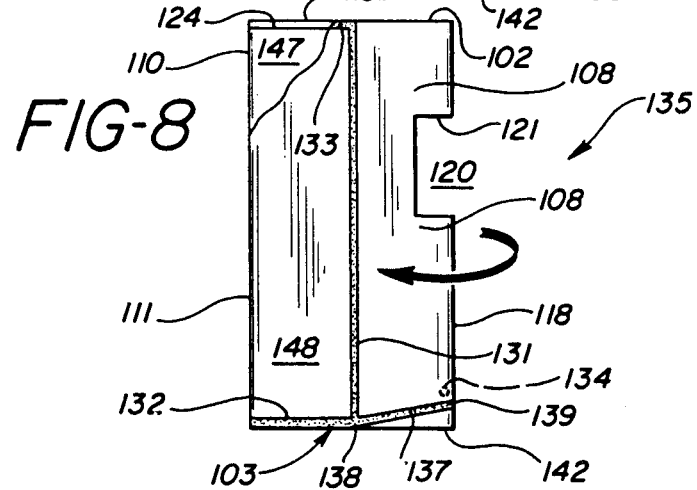

SURGICAL DRAPE WITH FLUID COLLECTION SYSTEM

This is a continuation, of application Ser. No. 115,012, filed Oct. 29, 1987 now abandoned.

FIELD OF THE INVENTION

The present invention relates to surgical drapes and particularly to surgical drapes comprising a fluid collection system designed to collect and drain away from the site of surgery substantial quantities of irrigating fluids. The surgical drape of the present invention is particularly useful in arthroscopic surgical procedures, particularly those involving the knee.

BACKGROUND OF THE INVENTION

A variety of surgical drapes, both reusable and disposable, has been provided by the prior art for draping operating tables, other operating room equipment, and patients who are about to undergo surgery. Several of these drapes are designed to handle and/or collect fluids, such as blood, amniotic fluid and irrigating liquids, which are commonly encountered in certain surgical and obstetrical procedures.

U.S. Pat. No. 3,791,382 to Collins discloses a surgical drape comprising a fenestrated main sheet and at least one pocket on the outer surface thereof to receive fluid runoff from the site of the surgical procedure. The pocket may be formed from a sheet of material which is attached to the main sheet along its side edges and in its lower region.

U.S. Pat. No. 4,105,019 to Haswell shows a fluid loss receptacle comprising a first sheet of flexible material having a first end portion forming a first pocket and a second end portion. The first pocket is formed by folding an edge of the first sheet upon itself and sealing it together. A second pocket is attached to the sheet above the first pocket.

U.S. Pat. No. 4,414,968 to Amin teaches a fenestrated surgical drape for cystoscopic procedures. The drape comprises a foldable pocket which is held open by a malleable frame so that the pocket can receive fluid runoff. The pocket has an upper portion with pleated side walls which help keep the pocket open and a lower funnel-like portion ending in a drain hole. A base may be coupled to the drain hole to conduct collected fluid to a waste container.

U.S. Pat. No. 4,559,937 to Vinson discloses a fenestrated craniotomy drape having a fluid collection bag with a screening means. The bag has a front panel, a back panel and closed left and right sides. It also has a first opening, an upper chamber, a lower chamber, and a screening means between the upper and lower chambers. The screening means is a line of adherence between the front and back panels. This line of adherence extends from side to side of the bag and has nonadhered gaps therein. The fluid collection bag is secured in place by adhering the top edge of its back panel to the upper surface of the drape below its fenestration. The top edge of the front panel of the bag is secured to an opening means comprising a rod of flexible material preferably encased in a fluid impervious plastic film. This opening means has ends which extend beyond the sides of the bag and these ends are preferably bent and adhered to the upper surface of the surgical drape. Fluid control rails comprising lengths of flexible tubing which are preferably encased in plastic film are sealed along their entire length to the upper surface of the drape, one such rail being placed on either side of the fenestration in the drape. The lower ends of these rails are secured over the top edge of the back panel of the fluid collection bag and extend to the open end of the bag and are supposed to direct fluids into the bag. The top edge of the front panel of the bag is not coextensive with the top edge of the back panel of the bag; as a result there is a "gap" at each side of the bag and there is a possibility of fluid leakage at the sides of the bag near its open end when the drape is in use. The fluid control rails are disclosed as being only about 10 mm high while the control means is disclosed as being about 17 mm high, as a result of which these structural components are ineffective in handling large amounts of fluids and preventing them from splashing onto the outer regions of the drape or OR personnel.

U.S. Pat. No. 4,598,458 to McAllester, filed on the same day as U.S. Pat. No. 4,559,937 and assigned to the same assignee, discloses a surgical drape comprising an upper surface, a surgical site, a fluid collection bag attached to said upper surface, fluid control rails alongside but spaced from the surgical site, and means for holding the bag open when the drape is being used. The fluid control rails channel fluid into the opening of the bag and are constructed of flexible, thick-walled tubing encased in a flexible sheet material. The opening means comprise a flexible polymeric foam rod also encased in a flexible sheet material.

U.S. Pat. No. 4,616,642 to Martin et al. discloses a Caesarean section drape comprising a base sheet having a primary operative area. A sheet of liquid-impervious plastic film overlies and is secured to the base sheet in at least part of the operative area and a sheet of first liquid absorbent material is secured to the outer surface of the liquid impervious film to form a laminated structure. The primary operative area has a region in which the base sheet, the liquid-impervious film and the sheet of first liquid absorbent material are coextensive. The coextensive region has a fenestration. A U-shaped region of supplemental absorbent material partially surrounds and is spaced from the fenestration. This U-shaped region of supplemental absorbent material may be retained within a pocket whose opening faces the fenestration. This pocket is formed from the edge portions of the plastic film/first absorbent material laminate which is folded back upon itself toward the fenestration.

U.S. Pat. No. 4,596,245 to Morris discloses a fenestrated surgical drape for endourological procedures comprising a main sheet, a series of tube holders and a fluid collection bag. The fluid collection bag is secured to the main sheet between the fenestration and side edge of the main sheet. There is one tubing holder on each side of the fenestration. Each of these tube holders has an extended end which extends into the fluid collection bag to direct fluid into the bag.

SUMMARY OF THE INVENTION

In accordance with one aspect of the present invention, there is provided a surgical drape comprising a main sheet and a fluid collection system. The fluid collection system comprises a liquid impervious bag, a portion of whose perimeter at its open end is secured to the upper surface of the main sheet near the primary operative area. Where the drape is provided with a fenestration, the bag is secured to the main sheet at a location between that fenestration and one of the edges of the main sheet. The fluid collection system further comprises a pair of fluid directing elements, each of which has a first portion and an adjoining remainder portion. An edge of each first portion is affixed to the drape at either side of the operative area or fenestration. The remainder portion of one of the fluid directing elements is secured to one portion of the peripheral edge of the fluid collection bag, while the remainder portion of the other of the fluid directing elements is secured to another portion of the peripheral edge of the bag. The inner surfaces of the ends of these two fluid directing elements are preferably coated with an adhesive and the adhesive is protected prior to use with a releaseable cover strip. The two strips of adhesive are applied to opposite sides of a patient's limb, e.g. the leg, in order to help secure the drape to the patient and assist in keeping the fluid collection bag open during manipulation of the extremity when surgery is being performed. The fluid directing elements include a support material which is sufficiently compressible to allow the said elements to be folded more or less flat against the surface of the drape in order to minimize bulk when the drape is folded and packaged. In addition, the support material must be inherently able of its own accord to recover from a compressed or folded state when the forces causing or maintaining such compression or folding are released. Thus, when the drape of the present invention is opened for use, the fluid directing elements thereof tend immediately, by virtue of the support material's inherent ability to recover from its compressed or folded state, to return to the configuration they had before having been folded and thus be substantially free of any compressed or folded regions which may have resulted from the folding operation. There is no need for the OR personnel to engage in difficult, tedious, time consuming manipulation or unfolding of the fluid directing elements in order to move them to their in-use position in which they are disposed upwardly in a position which is more or less perpendicular with respect to the main sheet of the drape.

In accordance with another aspect of the present invention there is provided a fluid collection system adapted to be secured to the upper surface of the main sheet of a surgical drape. This fluid collection system also comprises a fluid collection bag or reservoir and a pair of fluid directing elements. The fluid collection system may be made from a single sheet of fluid impervious material, such as, for example, polyethylene or the like, by a folding procedure to be described in more detail hereinafter. Briefly, however, the side marginal portions of a sheet of plastic are folded over and secured at their free peripheral edges to the upper surface of the sheet to thereby provide a pair of pockets. Strips of support material are inserted into the pockets to form a pair of fluid directing elements at the sides of the sheet. Marginal portions of the bottom edge of the sheet are secured together to form a fluid collection bag or reservoir. The bag is provided with an outlet so that fluids may be drained therefrom. This fluid collection system may be thereafter secured to a main sheet to provide a surgical drape capable of collecting and draining away large amounts of fluids which may be encountered during surgery.

In either of the aforementioned embodiments, the surgical drape preferably includes a layer or sheet of a thermoplastic—elastomeric polymer which is secured to the main sheet and is provided with a generally circular fenestration. Since the sheet material has elastic properties, the fenestration can be stretched to accept limbs of various sizes; after the drape has been positioned, the elastic material contracts to provide a fluid tight seal around the draped limb.

BRIEF DESCRIPTION OF THE DRAWINGS

The invention will be more clearly described by reference to the following detailed description and to the accompanying drawings in which:

FIG. 2 is a top plan view of the surgical drape of FIG. 1;

FIG. 3 is a cross-sectional view, with certain portions enlarged, taken along line 3—3 of FIG. 2;

FIG. 5 is an exploded perspective view showing the component parts of the surgical drape of FIG. 1;

FIG. 6 is a top plan view of a sheet of material from which the fluid collection means comprising the surgical drape of FIG. 1 may be made;

FIG. 7 is a view similar to that of FIG. 6 and showing the sheet of FIG. 6 with side portions thereof folded inwardly toward the center thereof;

FIG. 8 is a view showing the sheet of material of FIG. 7 after it has been folded substantially in half from side to side as indicated by the directional arrow;

DETAILED DESCRIPTION OF THE PREFERRED EMBODIMENT

Figure 11:
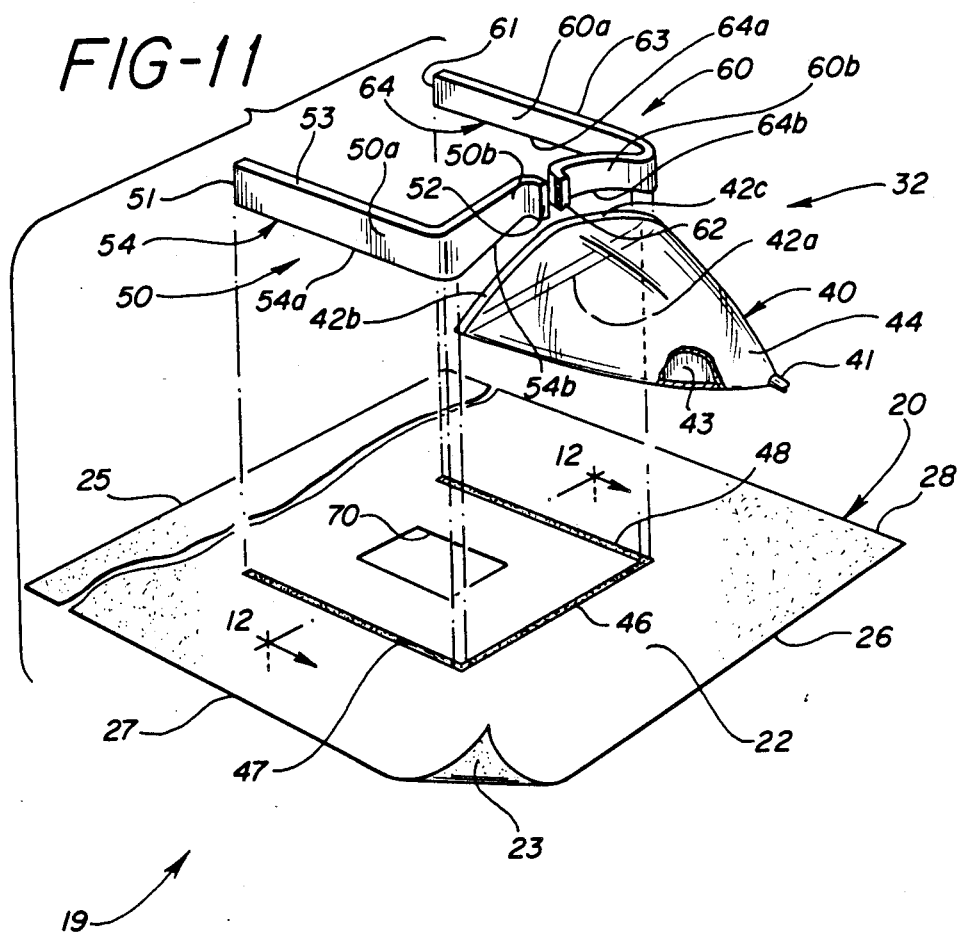
FIG. 11 is an exploded perspective showing the component parts of another embodiment of a surgical drape according to the present invention.
Figure 12:
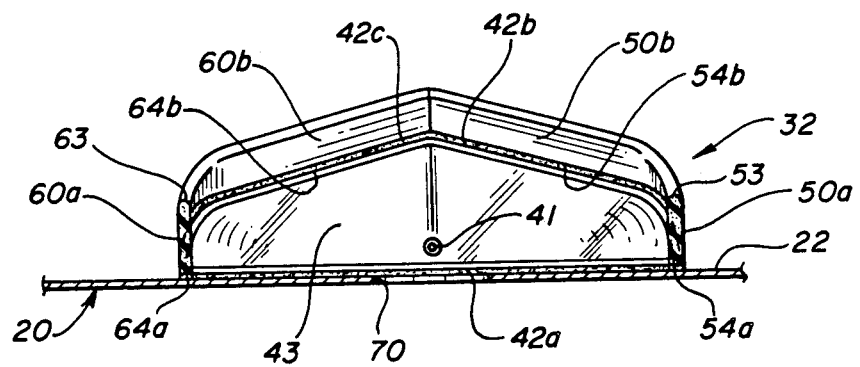
FIG. 12 is a cross-sectional view taken along line 12—12 of FIG. 11.

Referring now to FIGS. 11 and 12 of the accompanying drawings, there is shown one embodiment of a surgical drape of the present invention. Surgical drape 19 comprises a main sheet 20 and a fluid collection system 32. As shown in FIG. 11, main sheet 20 comprises an upper surface 22; a lower surface 23; a first end, or top edge 25; a second end, or bottom edge 26; and a pair of opposed, generally parallel side edges 27, 28.

Main sheet 20 preferably comprises a generally flexible, drapable nonwoven fabric. Alternatively, a sheet of generally flexible, drapable plastic film of suitable thickness may be used. Nonwoven fabrics are well-known and particularly suited as materials of construction for the main sheet and may be reinforced and/or rendered fluid repellent, e.g. with well-known fluorocarbon or silicone fluid repellents, if so desired.

Fluid collection system 32 comprises an open-ended receptacle means in the form of a pouch or bag 40 which is adapted to receive fluids such as blood or irrigation solutions which are encountered or used during surgery (hereinafter sometimes referred to as "operative fluids") and a pair of fluid directing elements 50,60 which, when the drape is being used, are adapted to collect said fluids and direct them into the open end of the receptacle means. Bag 40 comprises an inner surface 43, an outer surface 44 and an outlet means 41. Bag 40 also has a periphery at its open end, said periphery comprising a first portion 42a, a second portion 42b and a third portion 42c. First peripheral portion 42a is joined at one of its ends to second peripheral portion 42b and at the other of its ends to third peripheral portion 42c. The first peripheral portion 42a of bag 40 is secured to the upper surface of the main sheet so that bag 40 is located between bottom edge 26 and the region of the drape at which the surgery will be performed, said region usually being referred to in the surgical drape art as the "operative site". The preferred embodiment of the drape under discussion comprises a fenestrated region 70 extending through the thickness of the drape from its upper surface to its lower surface. Bag 40 is secured to the upper surface of the drape so that it is below the fenestrated region and in vertical alignment therewith, i.e. the bag is located between the fenestrated region of the drape and bottom edge 26 of main sheet 20. The open end of the receptacle means or bag 40 faces the fenestrated region so as to be positioned to receive fluids directed thereto from the operative site by the fluid directing elements.

Fluid directing elements 50,60 comprise hollow, generally elongated tubes, the interiors of which are provided with a support material such as, e.g., a polyester polyurethane foam, preferably in strip form. The tubes are most conveniently constructed from heat-sealable plastic, polyethylene film being preferred for this purpose. Other materials, such as strips of nonwoven fabric which have been treated to be fluid repellent, may be used in place of the plastic film, if desired.

As mentioned earlier, the support material for the interiors of the elongated tubes comprising fluid directing elements 50,60 must be compressible and recoverable from a compressed state. The support material must be sufficiently compressible so that a fluid directing element containing it may be readily folded against itself and against the surface of the main sheet of the drape so as to minimize the overall bulk of the surgical drape when it is folded and packaged. In addition, the support material must be inherently able of its own accord to recover from a compressed or folded state when the forces causing or maintaining such compression or folding are released. Thus, when the drape of the present invention is opened for use, the fluid directing elements thereof tend immediately, by virtue of the support material's inherent ability to recover from its compressed or folded state, to return to the configuration they had before having been folded and thus be substantially free of any compressed or folded regions which may have resulted from the folding operation. There is no need for the OR personnel to engage in difficult, tedious, time consuming manipulation or unfolding of the fluid directing elements in order to move them from their storage position which is more or less parallel to the plane of the main sheet to their upstanding, in-use position in which the fluid directing elements form a substantial angle with the plane of the main sheet. A support material which is particularly suited for use in the fluid directing elements 50,60 of the present invention is an open-celled polyester polyurethane foam having from about 30 to about 50 cells per linear inch (as counted visually with the aid of a magnifying glass), a density ranging from about 1.6 to about 2.2 lbs/ft$^3$, a compression set at 50% (as measured by ASTM D 3574-81, Test D) of from about 0 to about 20%; a tensile strength of from about 13 to about 30 lbs/in$^2$ (as measured by ASTM D-3574, Test E) and an indentation force deflection at 25% ranging from about 0.3 to about 0.6 lbs/in$^2$ (as measured by ASTM D-3574, Test B). Foams having the aforementioned characteristics are commercially available from various suppliers. Other support materials may be used in place of the aforementioned foam provided they have the aforementioned characteristics of compressibility and recovery from a compressed state.

Fluid directing element 50 is located on the left side of main sheet 20, i.e. between the fenestrated operative site and left side margin 27, while fluid directing element 60 is located on the right side of main sheet 20, i.e. between the fenestrated operative site and right side margin 28. Each of the directing elements is spaced a sufficient distance, e.g. about 6½ inches (16.5 cm) away from the nearest side edge of fenestration 70 so as not to interfere with the surgeon during performance of the surgical procedure.

Fluid directing element 50 has a first end edge 51, a second end edge 52, a generally elongated upper edge 53 and an opposed generally elongated lower side edge 54. Fluid directing element 50 comprises a first portion 50a adjoining a second, or remainder, portion 50b. First portion 50a has a lower side edge 54a and second, or remainder, portion 50b has a lower side edge 54b, these side edges 54a and 54b constituting the whole of lower side edge 54.

Fluid directing element 60 has the same structure as fluid directing element 50. It has a first end edge 61, a second end edge 62, a generally elongated upper edge 63 and an opposed generally elongated lower side edge 64. Fluid directing element 60 comprises a first portion 60a adjoining a second, or remainder, portion 60b. First portion 60a has a lower side edge 64a and second, or remainder, portion 60b has a lower side edge 64b, these side edges 64a and 64b constituting the whole of lower side edge 64.

The surgical drape shown in FIG. 11 is assembled in the following manner. First, peripheral edge portion 42a of bag 40 is secured to main sheet 20 with adhesive 46. The lower side edge 54a of first portion 50a of fluid directing element 50 is secured to the main sheet with adhesive 47. The lower side edge 64a of first portion 60a of fluid directing element 60 is secured to the main sheet with adhesive 48. The lower side edge 54b of remainder portion 50b of fluid directing element 50 is secured by an adhesive (not shown in FIG. 11) to the second peripheral portion 42b of bag 40. The lower side edge 64b of remainder portion 60b of fluid directing element 60 is secured by an adhesive (not shown in FIG. 11) to the third peripheral portion 42c of bag 40. It should be noted that the ends of fluid directing elements 50 and 60 shown near bag 40 in FIG. 11 have been curled out of their normal plane and toward the viewer so that their respective end edges 52 and 62 are clearly illustrated. Such curling need not occur when the drape is assembled in the manner just described. The fluid directing elements 50 and 60 have substantial height, for example, about 4 to 8 inches or even more, in the finished drape.

Although not illustrated in FIG. 11, the lower surface of main sheet 20 may, for certain situations, be provided with a coating of adhesive in the regions adjacent fenestration 70. This adhesive coating would be used to secure the drape to the patient's body at the site of surgery. When the drape is provided with such an adhesive, it is protected prior to use by a releasably adhered cover strip.

Referring now to FIGS. 1-5, there is shown a disposable surgical drape 18 comprising a main sheet 20 to the upper surface of which is secured a fluid collection system. The fluid collection system, illustrated generally by the numeral 35, is adapted to direct fluids, such as blood and irrigation fluids, which are encountered or used during surgery, away from the site of surgery and into a receptacle means where they can be conveniently retained prior to their periodic discharge to a waste container.

As best seen in FIG. 2, main sheet 20 has an upper surface 22; a lower surface 23; a first end, or top, edge 25; a second end, or bottom, edge 26; and a pair of opposed generally parallel side edges 27, 28. In the embodiment under discussion, and as can be seen in FIGS. 3 and 5, main sheet 20 has a generally rectangular opening or fenestration 70 formed therein. When drape 20 is intended for draping patient about to undergo surgery of the knee, fenestration 70 is conveniently located about half way between top edge 25 and bottom edge 26 and is centered from side-to-side of the drape.

It will be apparent to those skilled in the art that fenestration 70 may assume varying shapes and can be provided in other locations to suit special situations or for use in other surgical procedures. Typically, fenestration 70 is about 7 inches (17.78 cm) wide and about 9 inches (22.86 cm) long, but it will be understood that these dimensions are not critical to the present invention and may be varied.

It will be understood that FIG. 2 shows the surgical drape of the present invention with its fluid collection system 32 in its preuse configuration. The first portions 147a, 148a of fluid directing elements 147,148 lie in a plane which is generally parallel to the upper surface of the drape so that their lower surfaces face the upper surface of the drape. The second, or remaining, portions 147b and 148b of the fluid directing elements and the bag 144 to which they are attached have been flattened against the upper surface of the main sheet. In this preuse configuration, the surgical drape can be fan-folded longitudinally from each of its ends toward the center and transversely from each of its side edges toward the center to form a folded drape of reduced size. The drape in its folded configuration is thus easily packaged and ready for subsequent sterilization.

Still referring to FIG. 2, it will be seen that each of the fluid directing elements 147,148 extends beyond the upper end of the fenestrated operative site in the direction toward top edge 25 of main sheet 20. In use, elements 147,148 are lifted upwardly so as to be in a plane which forms a substantial angle with the plane of the main sheet and the bag is opened up so as to be in a position to receive fluids directed thereto by the fluid directing elements. The support material located in the interiors of elements 147,148 is preferably the same as that described in connection with the drape of FIGS. 11 and 12.

Referring now to FIGS. 6-10, there will be described a method for making a fluid collection system 135 comprising a single sheet 100 of generally flexible, drapable, liquid impermeable material. Sheet material 100 is preferably polyethylene film because it is inexpensive, highly liquid impervious and easily sealed with adhesives or by using well-known heat sealing or ultrasonic welding techniques. Sheet 100 has a top edge 102, a bottom edge 103, a pair of opposed, generally parallel side edges 104,105, an upper surface 107 and a lower surface 108. Sheet 100 has a first fold line 110 spaced inwardly about 9 inches (22.86 cm) from its left side edge 104 and a second fold line 111 spaced inwardly about 9 inches (22.86 cm) from its right side edge 105, these fold lines running substantially parallel to the side edges of the sheet and to each other. Sheet 100 thus comprises a central portion 114, an adjoining left side marginal portion 113 and an adjoining right side marginal portion 115. Left side marginal portion 113 joins central portion 114 along fold line 110, while right side marginal portion 115 joins the central portion along fold line 111. Sheet 100 also has a longitudinal centerline 118, seen in FIG. 7, running from top edge 102 to bottom edge 103 and parallel to side edges 104,105.

As used herein, the term "forward fold" means a fold around a fold line in such manner that the upper surface of one portion of the material being fold is brought toward the upper surface of another portion of the material being folded.

In an actual full size surgical drape designed for use in arthroscopic procedures, fluid collection system 135 may be made by folding, in the manner hereinafter described, a rectangular sheet 100 of polyethylene which is 2.5 mils thick, whose side edges 104,105 are about 36 inches (91.44 cm) in length and whose top and bottom edges 102,103 are about 58 inches (147.32 cm) in length. A substantially rectangular fenestration 120 measuring about 7 inches (17.78 cm) in its direction parallel to the top and bottom edges 102,103 of sheet 100 and about 9 inches (22.86 cm) in its direction parallel to the side edges 104,105 is provided in sheet 100. The upper edge 121 of the fenestration is spaced about 9 inches (22.86 cm) from upper edge 102 of sheet 100. The fenestration is centered between the side edges of sheet 100 so that it is bisected longitudinally by centerline 118. A small circular hole 134 is provided in sheet 100 at a location which is near the intersection of bottom edge 103 and centerline 118 of the sheet. The purpose of hole 134 is to accommodate a fluid outlet in the final fluid collection system.

Left side marginal portion 113 is forward folded around fold line 110, as indicated by phantom arrow "A" in FIG. 6, so that its upper surface is brought into face-to-face contact with the upper surface of central portion 114. Marginal portion 113 is secured, preferably by heat sealing, to central portion 114 along a line of securement 122 running adjacent side edge 104 (which, owing to the aforementioned folding step, is now located between fold line 110 and centerline 118) and along a line of securement 123 running adjacent bottom edge 113a of marginal portion 113 to form a side pocket 127. A strip 129 of the previously described polyester polyurethane foam about 34 inches (86.36 cm) long, 8 inches (20.32 cm) wide, and 0.25 inch (0.63 cm) thick is inserted into pocket 127 as illustrated in the upper left hand corner of FIG. 7. Marginal portion 113 is then secured to central portion 114, again preferably by heat sealing, along a line of securement 124 (see FIG. 8) running adjacent top edge 113b of marginal portion 113 so as to completely enclose foam strip 129 in side pocket 127. In other words, after the left marginal portion 113 is folded around fold line 110, it is secured to central portion 114 by heat sealing it in the regions adjacent its theretofore unattached side edge 104, top edge 113b, and bottom edge 113a to thereby form a closed pocket which encloses and retains foam strip 129.

Right side marginal portion 115 is then forward folded around fold line 111, as indicated by phantom arrow "B" in FIG. 6, so that its upper surface is brought into face-to-face contact with the upper surface of central portion 114. Marginal portion 115 is secured, preferably by heat sealing, to central portion 114 along a line of securement 131 running adjacent side edge 105 (which, owing to the aforementioned folding step, is at this stage located between fold line 111 and centerline 118) and along a line of securement 132 running adjacent bottom edge 115a of marginal portion 115 to form a pocket 128. A strip 130 of polyester polyurethane foam having the same dimensions as strip 129 is inserted into pocket 128. Marginal portion 115 is then secured to central portion 114 by heat sealing along a line of securement 133 running adjacent upper edge 115b so as to completely enclose foam strip 130 within pocket 128.

As will be seen hereinafter, pocket 127 having foam strip 129 enclosed therein comprises one fluid directing element 147; correspondingly, pocket 128 having foam strip 130 enclosed therein comprises another fluid directing element 148.

It will be seen by referring to FIG. 7, that after pockets 127 and 128 have been formed at the sides of central portion 114, original bottom edge 103 of sheet 100 has two free interior edge portions 141 and 142. First interior edge portion 141 extends along edge 103 from centerline 118 to line of securement 122 while second interior edge portion 142 extends along edge 103 from centerline 118 to line of securement 131. The length of interior edge portions 141 and 142 are substantially equal.

Sheet 100, in the configuration shown in FIG. 7, is then folded in half so that the upper surface of central portion 114 on the right hand side of centerline 118 comes into face-to-face contact with the upper surface of central portion 114 on the left hand side of centerline 118 and second interior edge portion 142 overlies first interior edge portion 141. This provides a first folded unit 135, shown in FIG. 8, having a right side edge defined by centerline 118 and a left side edge defined by the now aligned fold lines 110 and 111, these latter lines being the outer edges, respectively, of pockets 127 and 128 shown in FIG. 7.

The portions of sheet 100 adjacent first interior edge 141 and second interior edge 142 of first folded unit 135 are then heat sealed along a line of securement 137 which extends from the point 138 at which line of securement 131 joins line of securement 132 to a point 139 on the right side edge 118 of first folded unit 135. This line of securement may be parallel to and adjacent edge portions 141,142 of unit 135. As illustrated in FIG. 8, it is preferred, however, that line of securement 137 extend at a slight angle from the point of juncture 138 to point 139. In the aforementioned actual full size drape, point 139 is located on edge 118 about 3 inch e.g. (7.62 cm) from bottom edge 103. When this heat sealing step has been completed, there is formed a fluid tight bag means 144 (best seen in FIG. 4) at the bottom region of folded sheet 100 which is adapted to collect operative fluids. The small unsealed triangular portion lying outwardly of line of securement 137 may cut off, if desired. Alternatively, folded unit may be turned inside-out in order to dispose the triangular portion interiorly of bag means 144.

Figure 10:
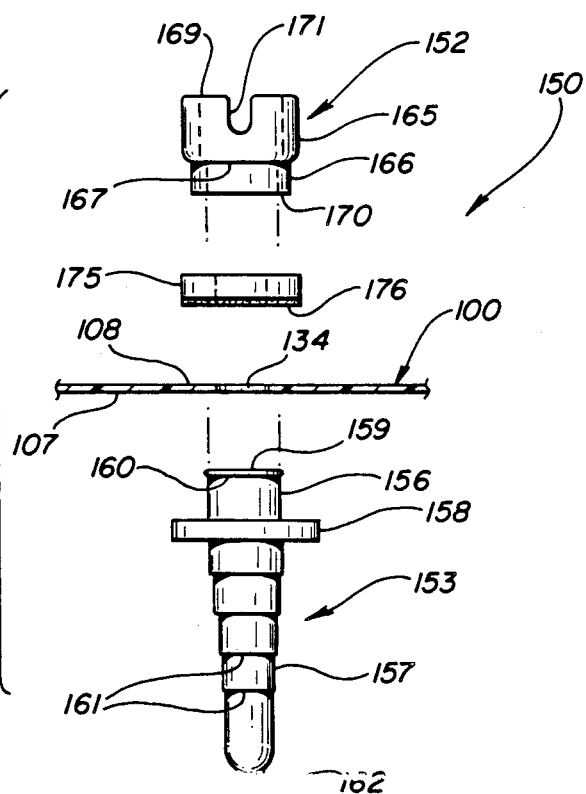
FIG. 10 is an exploded elevational view, partially in cross-section, showing the drainage port in the collection bag of the fluid collection system.

Bag 144 of fluid collection system 35 is provided with an outlet so that fluid may be drained therefrom on a periodic or continuing basis as may be desired at the time of use. As seen in FIG. 10, outlet 150 comprises an inner fitting 152 and an outer fitting 153. Fittings 152 and 153 are hollow throughout their lengths. Outer fitting 153 is a relatively rigid tubular member which may be made, for example by injection molding, from a polymeric resin such as polypropylene. Fitting 153 comprises a substantially circular first portion 156, a second portion 157 and an enlarged, generally circular flange 158 which is located toward first end 159 of the fitting. First portion 156 terminates in a smooth surfaced rim 160. Second portion 157 carries a plurality of tubing barbs 161 on its outer surface in at least part of the region between flange 158 and its tip 162. First portion 156 has (except for rim 160) a substantially uniform outside diameter throughout its length. Second portion 157 is slightly tapered from flange 158 toward tip 162 so as to be adapted to more readily accept a length of hollow drainage tubing by which fluid accumulating in bag 144 is conducted to a waste container.

Inner fitting 152 is a relatively rigid, generally tubular member which is preferably made from the same material as outer fitting 153. Fitting 152 comprises a first substantially circular peripheral wall 165 adjacent its upper end 169 and a second substantially circular peripheral wall 166 adjacent its lower end 170. In addition, fitting 152 has a circumferential shoulder 167 where peripheral wall 165 joins peripheral wall 166.

The interior hollow portion of portion 166 is substantially circular in cross-section and has a diameter which is slightly less than the outside diameter of first portion 156 comprising outer fitting 153. As will be seen in the top center of FIG. 10 and in the lower left hand corner of FIG. 4, inner fitting 152 has a plurality of cut-out portions 171 in its upper peripheral wall 165. These cut-away portions allow for the passage of fluids in the event end 169 of fitting 152 becomes partly clogged, e.g. with clotted blood or the like during use.

Outlet 150 is secured to main sheet 100 in the lower region thereof which forms bag 144 in the following manner. First portion 156 of outer fitting 153 is inserted through hole 134 in sheet 100. Since the diameter of portion 156 is larger than that of hole 134, the regions of sheet 100 around hold 134 are brought into tight frictional engagement with the outer surface of portion 156. A compressible foam washer 175 having a circular central opening whose diameter is less than the outside diameter of first portion 156 is coated on its lower surface with a fluid impervious adhesive 176, passed over first portion 156 and brought into contact with the lower surface 108 of sheet 100. Inner fitting 152 is then slipped over first portion 156 of outer fitting 153 and pushed downwardly so that the outer surface of end portion 156 is in tight frictional engagement with the inside surface of circular wall 166, rim 160 of first portion 156 is engaged with the lower inner surface of peripheral wall 165, and washer 175 is compressed between lower surface 108 of sheet 100 and shoulder 167 of inner fitting 156. This procedure effects a fluid tight seal between outlet 150 and sheet 100.

Referring now to FIG. 5, there is shown an exploded perspective view of surgical drape 18. This drape is especially useful in arthroscopic surgery of the knee. The drape comprises the fluid collection system 35 described earlier with reference to FIGS. 6-10. In FIG. 5, fluid collection system 35 has been illustrated in its "opened-up", more or less three-dimensional configuration it assumes in actual use. It will be noticed that a strip of adhesive 186 (FIG. 5A) has been placed on the inwardly facing surface 116 of fluid directing element 148 near its lower end edge 148c. The term "inwardly facing surface" refers to that surface of fluid directing element 148 which, as illustrated in FIG. 5, faces toward central portion 114 of sheet 100 when the fluid directing element is turned toward the central portion 114. Adhesive strip 186 is protected prior to use by a releasably adhered cover strip 187. A corresponding strip of adhesive is placed on the inwardly facing surface 117 of fluid directing element 147 and is covered with a corresponding releasably adhered cover strip. A reinforcing means 190 in the form of a strip of plastic such as polyethylene or polyvinylchloride is secured, for example with any suitable adhesive, transversely of line of securement 137 along which interior edges 141,142 have been joined to each other. The reinforcing means 190 is located near that end of line of securement 137 which is near the lower edges 147c and 148c of fluid directing elements 147 and 148, respectively.

The arthroscopic drape of FIG. 5 comprises a main sheet 20, panel or sheet 75, fluid collection system 35, a tubing holder 80 and a pair of clipping tabs 85,85. Main sheet 20, which has been described earlier herein, has a length of about 120 inches (304.8 cm), a width of about 86 inches (218 cm), and is provided with a fenestration 70 which, in the arthroscopic drape being discussed, is about 7 inches (17.78 cm) wide and about 9 inches (22.85 cm) long. The drape comprises a panel 75 comprising a relatively thin sheet of thermoplastic-elastomeric polymer available under the trademark KRATON. The panel 75 comprises a centrally located, generally circular fenestration 77 about 2.5 inches (6.35 cm) in diameter. This panel is secured, for example, with the use of an adhesive 76, to the upper surface of main sheet 20 so that its fenestration 77 is axially aligned with fenestration 70 in the main sheet. Thus, regions of the material comprising panel 75 will lie inwardly of the edges of fenestration 70 in the main sheet. In the case of the arthroscopy drape under discussion, the adhesive 76 which secures panel 75 to main sheet 20 is applied to that region of the main sheet which lies immediately adjacent the peripheral edges of its fenestration 70 and which extends outwardly to the outer peripheral edges of panel 75.

Figure 1:
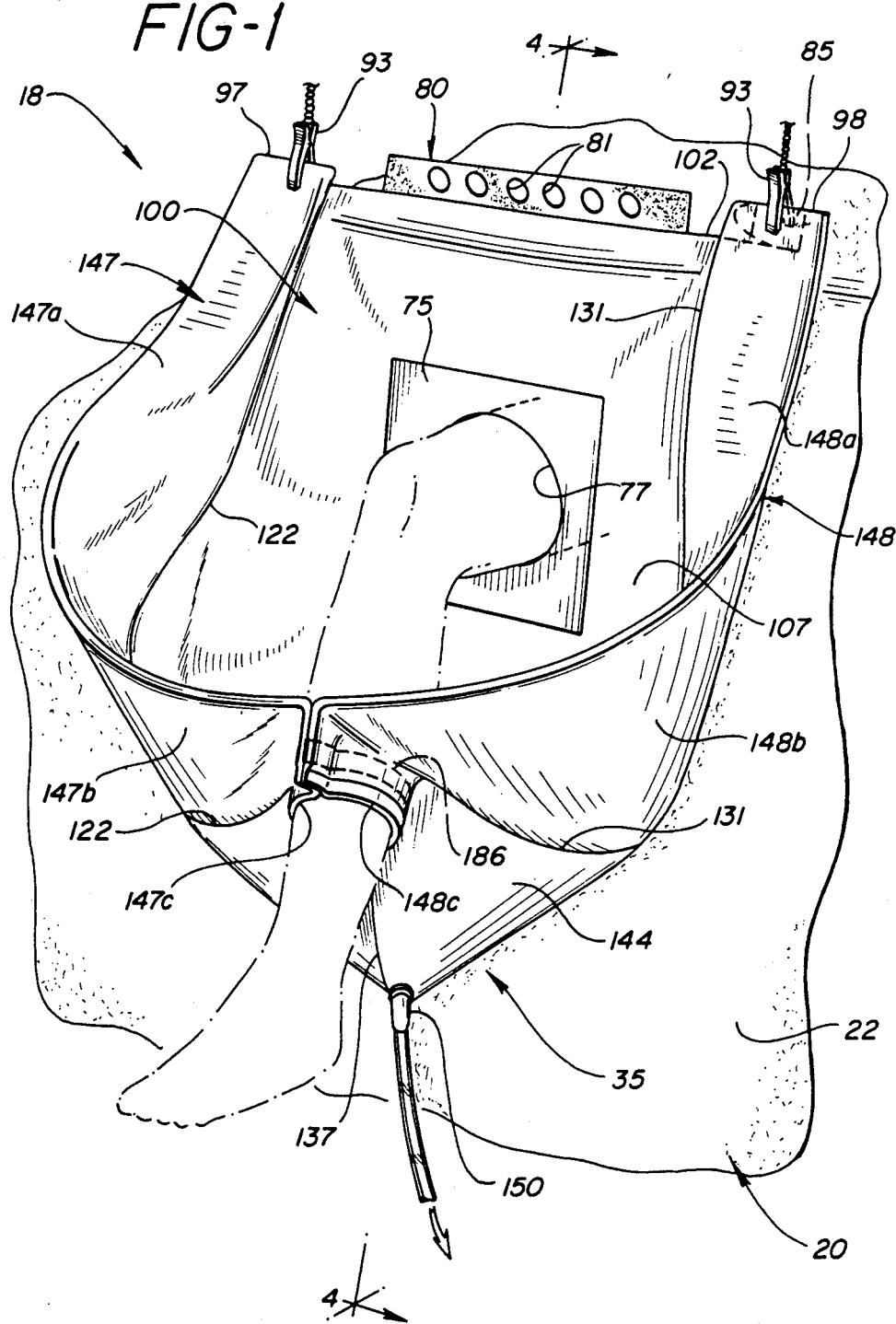
FIG. 1 is a perspective view of one embodiment of a surgical drape of the present invention placed over the leg of a patient about to undergo surgery of the knee.
Figure 4:
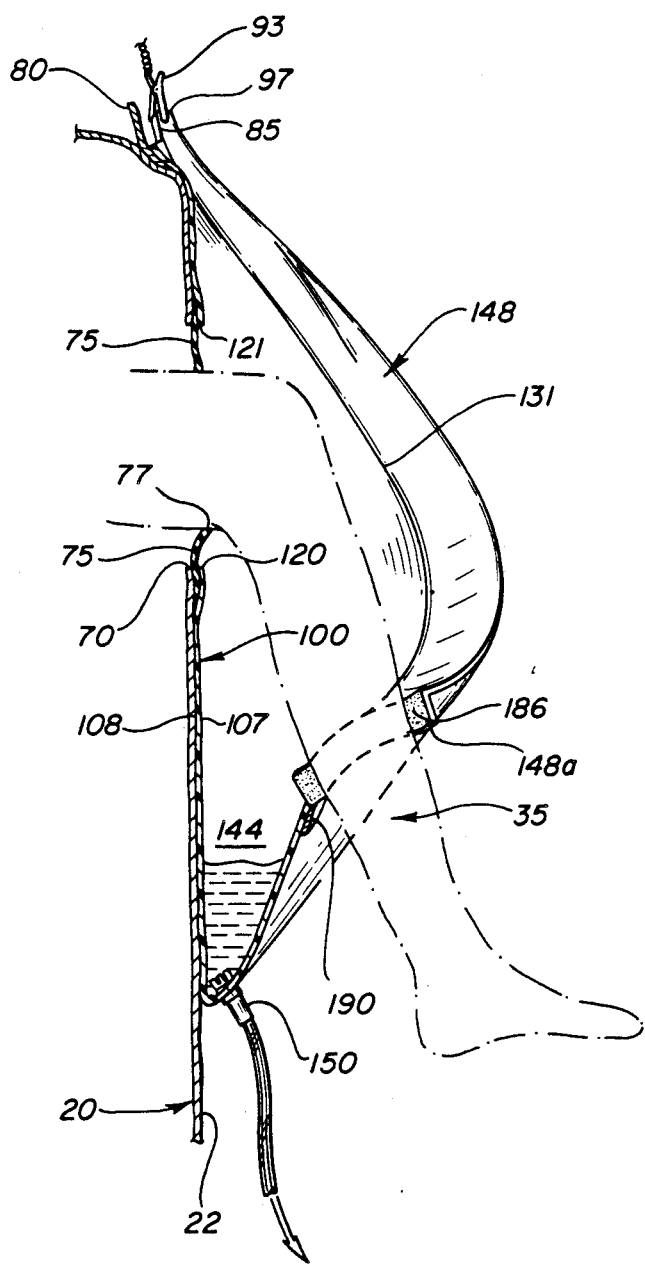
FIG. 4 is a cross-sectional view taken along line 4—4 of FIG. 1.
Figure 9:
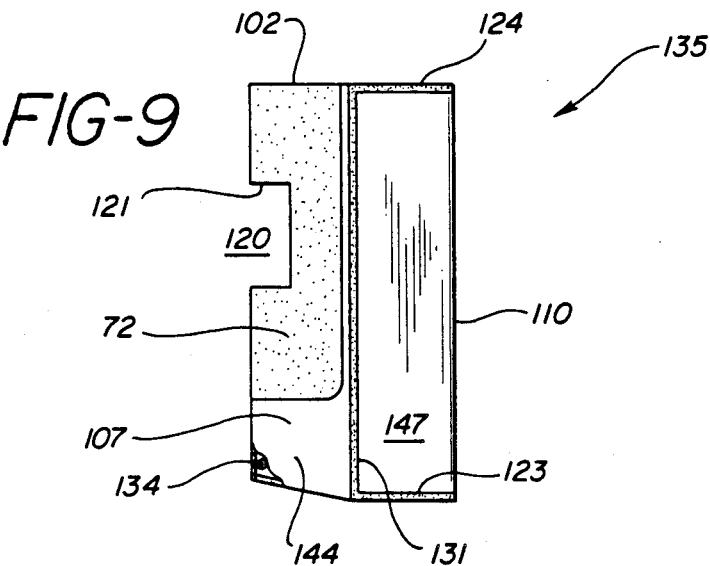
FIG. 9 is a view of the folded sheet shown in FIG. 8 after it has been folded inside out upon itself and turned so that the fenestration is on the left side as viewed by the reader.

After the panel 75 is attached to the main sheet, a coating of adhesive 72 is applied to the lower surface of fluid collection system 35 in the area thereof which is indicated by stippling in FIG. 9 and the fluid collection system is secured to the main sheet so that its fenestration 120 is in axial alignment with fenestrations 70 and 77 in main sheet 20 and panel 75, respectively. It will be observed that the fluid directing elements 147,148 of fluid collection system 35 are attached to main sheet 100 along lines of securement 122 and 131, respectively, but are otherwise left free of attachment to the drape. Bag 144 is an integral part of sheet 100 after the sheet has been folded but is preferably left free of further attachment to the drape.

A tubing holder 80 comprising, e.g., a strip of nonwoven material with a plurality of holes 81 therein, is adhesively secured to the drape between the upper surface of main sheet 20 and the lower surface of fluid collection system 35 at its upper edge 102. A clipping tab 85 is placed at each end of tubing holder 80, preferably in the same position as the tubing holder. As shown in FIG. 5, the tubing holder and the clipping tabs can be formed from a strip of nonwoven, plastic or the like, material. Still referring to FIG. 5, the arthroscopy drape optionally comprises an annular, gasket-like reinforcing element 90 which, if employed, preferably includes narrow strips 91 of double faced adhesive tape placed at the marginal top, bottom and side edges of panel 75. These adhesive strips are secured to the outer edges of panel 75 by the adhesive on their lower surfaces; and they are secured to the lower surface of the fluid collection system by the adhesive on their upper surfaces. In another optional feature, and as seen in FIG. 5, the lower surfaces of fluid directing elements 147,148 are provided with adhesive strips 95 near the ends 97,98 thereof which are located at the top edge of sheet 100. If employed, these adhesive areas 95,95 are protected prior to use by releasably adhered cover strips. During use of the drape, portions of the fluid directing elements 147,148 near top edge 102 may be "doubled over" to provide a double thickness thus providing the fluid directing elements with an increased ability to maintain their generally upstanding, in-use configuration.

The drape of FIGS. 1–5 is used as follows. Drape 18 is applied to a patient about to undergo a arthroscopic surgery of the knee in the following manner. The operating table is arranged so that its leg support portion is inclined downwardly so as to form an angle with the horizontal, or body supporting, portion thereof. The patient lies on the table so that his leg to be operated on hangs over the horizontal main portion of the table where it will be ultimately supported by the inclined leg support portion of the table. The drape is held by a nurse with the drape's lower surface 108 facing the patient and with its upper surface 107 facing the nurse. An assistant places the patient's foot through fenestration 77 in panel 75 and the drape is moved upwardly along the patient's leg to a position which is above the patient's knee and in which the elastomeric-thermoplastic material constituting panel 75 surrounds the patient's thigh region. The fluid directing elements 147,148 are unfolded and lifted from their storage position and brought to their upstanding, in-use position in which they form a substantial, more-or-less perpendicular angle with the plane of the main sheet. The ends 97,98 of the fluid directing elements 147,148 can be clipped, as with towel clamps 93,93, to clipping tabs 85,85; this assists in holding them in their desired position. Before clamping, and if desired, the fluid directing elements may be doubled over (as shown in the upper left hand corner of FIG. 5) at their ends 97,98 to provide the aforementioned double thickness which provides increased rigidity and reduces the possibility of the fluid directing elements being accidentally moved during the surgical procedure. Adhesive portions 95 at the ends of the fluid directing elements may be used to hold the doubled over portions in position. The bag portion 144 of the fluid collection system is opened up and the ends of the fluid directing elements are secured around the lower leg of the patient, in the manner shown in FIGS. 1 and 4, by the use of adhesive portions 186,186. The end of outlet 150 is cut off to provide fluid access to its interior. One end of a length of tubing is attached to outlet 150 and the other end is attached to a suction device leading to a waste container. When so placed on the patient, the fluid directing elements help prevent splashing of operative fluids on the outer periphery of the drape and on operating room personnel. The fluid directing elements direct the operative fluids into bag 144 from which they are drained to the waste container.

In the absence of adhesive strips 186,186, the ends of the fluid directing elements may be placed around the lower leg of the patient and held in place with clamps.

What is claimed is:

1. A fluid collection system comprising a sheet of generally flexible, fluid-impervious material, said sheet having an upper surface, a lower surface, a top edge, a bottom edge, a pair of generally opposed side edges, a longitudinal centerline running parallel to said side edges, a first fold line between said centerline and a first of said side edges, a second fold line between said centerline and the second of said side edges, a first marginal portion between said first fold line and said first side edge, a second marginal portion between said second fold line and said second side edge, and a central portion between said first marginal portion and said second marginal portion, said first marginal portion being forward folded around said first fold line and said second marginal portion being forward folded around said second fold line so that their respective upper surfaces face the upper surface of said central portion, said first and second marginal portions being secured to said central portion along lines of securement running adjacent their free edges to form a first pocket on one side of said central portion and a second pocket on the other side of said central portion, each of said pockets forming fluid directing elements and comprising a material which is compressible and recoverable from a compressed state, said first pocket comprising an upper edge, a lower edge, an outer longitudinal edge defined by said first fold line and an inner longitudinal edge between its said outer longitudinal edge and said centerline, said second pocket comprising an upper edge, a lower edge, an outer longitudinal edge defined by said second fold line and an inner longitudinal edge between its said outer edge and said centerline, the bottom edge of said central portion comprising first and second interior edge portions, the first interior edge portion extending from said centerline toward the inner longitudinal edge of said first pocket and the second interior edge portion extending from said centerline toward the inner longitudinal edge of said second pocket, said sheet being folded around said centerline to form a first folded unit in which said first and second interior edge portions are positioned one on top of the other and in which the outer longitudinal edges of said first and second pockets are aligned with each other, the portions of said central portion which are adjacent said first and second interior edge portions being secured together in liquid tight relationship to thereby form a generally centrally located reservoir for fluids at the bottom of said folded sheet, the respective bottom edges of each of said pockets being free of attachment to each other.

2. A fluid collection system according to claim 1 wherein the inner surface of each of said pockets is coated with an adhesive in a region adjacent its bottom edge.

3. A fluid collection system according to claim 2 wherein the adhesive on the inner surface of each of said pockets is protected prior to use with a releaseable liner.

4. A fluid collection system according to claim 1 further comprising reinforcing means applied across the line of securement of said first and second interior edge portions in the regions near the bottom edges of said first and second pockets.

5. A fluid collection system according to claim 1 wherein said sheet is a plastic film.

6. A fluid collection system according to claim 5 wherein said plastic film comprises polyethylene.

7. A surgical drape comprising a main sheet of generally flexible, drapable material having affixed thereto the fluid collection system of claim 1.

8. A surgical drape according to claim 7 wherein said main sheet comprises a peripheral edge and a fenestration, said fluid collection system comprises a fenestration, and said fenestrations each define a plane, said pair of planes being alignable parallel to each other while a single perpendicular axis passes through the center of each of said fenestrations.

9. A surgical drape according to claim 8 wherein the reservoir means of said fluid collection system is located between the regions of said fenestrations and said peripheral edge of the main sheet.

10. A surgical drape according to claim 8 wherein there is a reinforcing material between said main sheet and said fluid collection system in the regions surrounding said fenestrations.

11. A surgical drape according to claim 10 wherein the fenestration in said fluid collection system has substantially the same dimensions as the fenestration in said main sheet and said reinforcing material comprises a fenestration which has an area which is smaller than the areas of the fenestrations in the main sheet and the fluid collection system.

12. A surgical drape according to claim 11 wherein said reinforcing material comprises a thermoplastic elastomeric polymer and the fenestration in said fluid collection system is circular in configuration.

13. A surgical drape comprising:
(a) a main sheet of generally flexible, drapable material having an upper surface, a lower surface and a periphery comprising a top edge, a bottom edge and a pair of opposed side edges,
(b) a primary operative area located inwardly of the periphery of said main sheet,
(c) a liquid impervious bag means having an inner surface, an outer surface, an open end comprising a periphery and being adapted to admit fluids into the interior thereof, a closed end, and means for draining fluids therefrom, the periphery of said bag comprising a first peripheral portion, a second peripheral portion and a third peripheral portion; the first peripheral portion of said bag means being secured to the upper surface of the main sheet at a location between the primary operative area and an edge of said main sheet;
(d) a pair of generally elongated, fluid directing elements, which comprises a material that is compressible to and recoverable from, a compressed state, each of said fluid directing elements comprising a first portion and adjoining remainder portion; the lower side edge of each of the first portions of said fluid directing elements being secured to the main sheet in spaced apart relationship near the primary operative area; the lower side edge of the remainder portion of the first fluid directing element being secured to the second peripheral portion of said bag means and the lower side edge of the remainder portion of the second fluid directing element being secured to the third peripheral portion of said bag means.

14. A surgical drape according to claim 13 wherein said main sheet comprises a fenestration.

15. A surgical drape according to claim 14 wherein the lower surface of the main sheet is coated with an adhesive in the regions adjacent said fenestration.

16. A surgical drape according to claim 15 wherein said adhesive coating is protected prior to use with a releasably adhered cover strip.

17. A surgical drape according to claim 14 further including a layer of thermoplastic-elastomeric polymer secured to said main sheet and overlying the fenestration in said main sheet.

18. A surgical drape according to claim 14 wherein said main sheet fenestration defines a first plane and said drape further includes a layer of thermoplastic-elastomeric polymer secured to said main sheet, said layer comprising a fenestration that defines a second plane, said first and second planes being alignable parallel to each other while a single perpendicular axis passes through the center of each of said fenestrations.

19. A surgical drape according to claim 18 wherein said liquid impervious bag means further comprises a fenestration that defines a third plane that is alignable parallel to said first and second planes while a single perpendicular axis passes through the center of each of said fenestrations.

20. A surgical drape according to claim 13 wherein the inner surfaces of the ends of said fluid directing elements located near said bag means are coated with an adhesive.

21. A surgical drape according to claim 20 wherein said adhesive coatings are protected prior to use with releasably adhered cover strips.

22. A method of making a fluid collection system for a surgical drape comprising:
(a) providing a sheet of generally flexible, drapable, fluid impervious material; said sheet having an upper surface, a lower surface, a top edge, a bottom edge, a pair of generally opposed side edges, a longitudinal centerline running parallel to said side edges, a first fold line between said centerline and a first of said side edges, a second fold line between said centerline and the second of said side edges, a first marginal portion between said first fold line and said first side edge, a second marginal portion between said second fold line and said second side edge, and a central portion between said first marginal portion and said second marginal portion,
(b) folding said first marginal portion in a forward fold around said first fold line;
(c) placing a support material beneath the folded first marginal portion;
(d) securing the free edges of the folded first marginal portion to the underlying regions of the main sheet to thereby provide a first pocket which has an outer longitudinal edge corresponding to said first fold line and an inner longitudinal edge and which encloses said support material;
(e) folding said second marginal portion in a forward fold around said second fold line;
(f) placing a support material beneath the folded second marginal portion;
(g) securing the free edges of the folded second marginal portion to the underlying regions of the main sheet to thereby provide a second pocket which has an outer longitudinal edge corresponding to said second fold line and an inner longitudinal edge and which encloses said support material;
(h) folding said sheet around said longitudinal centerline so that said first and second pockets are in substantial alignment; and
(i) securing together the bottom edge portions of said sheet which extend from said centerline toward the interior edges of said first and said second pockets.

23. A method according to claim 22 wherein said sheet of fluid impervious material comprises a plastic film.

24. A method according to claim 23 wherein said plastic film is polyethylene.

25. A method according to claim 23 wherein said securing steps are done by heat sealing.

* * * * *